United States Patent
Toursel et al.

(10) Patent No.: US 10,465,159 B2
(45) Date of Patent: Nov. 5, 2019

(54) OPTIMISED METHOD FOR BREAKING CHLORELLA WALLS BY MECHANICAL CRUSHING

(71) Applicant: Corbion Biotech, Inc., South San Francisco, CA (US)

(72) Inventors: Beatrice Toursel, Gonnehem (FR); Francois Delannoy, Allouagne (FR); Samuel Patinier, Quesnoy-sur-Deule (FR)

(73) Assignee: CORBION BIOTECH, INC., South San Francisco, CA (US)

( * ) Notice: Subject to any disclaimer, the term of this patent is extended or adjusted under 35 U.S.C. 154(b) by 877 days.

(21) Appl. No.: 14/902,430

(22) PCT Filed: Jul. 3, 2014

(86) PCT No.: PCT/FR2014/051704
§ 371 (c)(1),
(2) Date: Dec. 31, 2015

(87) PCT Pub. No.: WO2015/001261
PCT Pub. Date: Jan. 8, 2015

(65) Prior Publication Data
US 2016/0376542 A1   Dec. 29, 2016

(30) Foreign Application Priority Data

Jul. 4, 2013 (FR) .................... 13 56577

(51) Int. Cl.
*C12N 1/06* (2006.01)
*B02C 25/00* (2006.01)
(Continued)

(52) U.S. Cl.
CPC ............. *C12N 1/066* (2013.01); *B02C 17/16* (2013.01); *B02C 17/20* (2013.01); *B02C 23/00* (2013.01);
(Continued)

(58) Field of Classification Search
CPC .......... C12N 1/12; C12N 1/066; C12M 47/06; C12M 21/02; B02C 17/20; B02C 17/16
(Continued)

(56) References Cited

U.S. PATENT DOCUMENTS

| 3,983,008 A | 9/1976 | Shinozaki et al. |
| 4,564,526 A | 1/1986 | Takashima |
| 5,330,913 A | 7/1994 | Nakayama |
| 5,547,699 A | 8/1996 | Iizuka et al. |
| 5,792,631 A | 8/1998 | Running |
| 5,885,564 A | 3/1999 | Zastrow et al. |

(Continued)

FOREIGN PATENT DOCUMENTS

| CN | 101352249 | 1/2009 |
| CN | 101449827 A | 6/2009 |

(Continued)

OTHER PUBLICATIONS

What is Specific Gravity?; by "Nissa Garcia" retrieved date: Sep. 19, 2018.*

(Continued)

*Primary Examiner* — Shelley M Self
*Assistant Examiner* — Mohammed S. Alawadi
(74) *Attorney, Agent, or Firm* — Leydig, Voit & Mayer

(57) ABSTRACT

Disclosed is a method of mechanically crushing microalgae cells of the genus *Chlorella* at an industrial scale, the mechanical crushing being carried out in a horizontal ball mill system. In the method, the balls have an apparent density of between 2 and 3.5 kg/l, the filling rate of the crushing chamber is greater than or equal to 80%, and preferably greater than or equal to 85%, and the mechanical crushing is carried out continuously by a series of successive passes.

12 Claims, 4 Drawing Sheets

(51) Int. Cl.

| | |
|---|---|
| *B02C 23/02* | (2006.01) |
| *B02C 23/00* | (2006.01) |
| *B02C 17/16* | (2006.01) |
| *B02C 17/20* | (2006.01) |
| *C12M 1/00* | (2006.01) |
| *C12N 1/12* | (2006.01) |

(52) U.S. Cl.
CPC .............. *B02C 23/02* (2013.01); *B02C 25/00* (2013.01); *C12M 21/02* (2013.01); *C12M 47/06* (2013.01); *C12N 1/12* (2013.01)

(58) Field of Classification Search
USPC .......................................................... 241/30
See application file for complete search history.

(56) References Cited

U.S. PATENT DOCUMENTS

| | | | |
|---|---|---|---|
| 2004/0164194 A1* | 8/2004 | Reed ...................... | B02C 17/16 241/172 |
| 2007/0099280 A1 | 5/2007 | Barclay | |
| 2010/0297292 A1 | 11/2010 | Brooks et al. | |
| 2010/0297295 A1 | 11/2010 | Brooks et al. | |
| 2010/0297296 A1 | 11/2010 | Brooks et al. | |
| 2010/0297323 A1 | 11/2010 | Brooks et al. | |
| 2010/0297325 A1 | 11/2010 | Brooks et al. | |
| 2010/0297331 A1 | 11/2010 | Brooks et al. | |
| 2010/0303957 A1 | 12/2010 | Brooks et al. | |
| 2010/0303961 A1 | 12/2010 | Brooks et al. | |
| 2010/0303989 A1 | 12/2010 | Brooks et al. | |
| 2010/0303990 A1 | 12/2010 | Brooks et al. | |
| 2012/0128851 A1 | 5/2012 | Brooks et al. | |
| 2013/0122180 A1 | 5/2013 | Brooks et al. | |
| 2016/0177257 A1 | 6/2016 | Patinier | |
| 2016/0324167 A1 | 11/2016 | Brooks et al. | |
| 2018/0139994 A1 | 5/2018 | Brooks et al. | |

FOREIGN PATENT DOCUMENTS

| | | |
|---|---|---|
| CN | 10 1756300 A | 6/2010 |
| CN | 101817738 | 9/2010 |
| CN | 102304168 | 1/2012 |
| CN | 102433015 | 5/2012 |
| CN | 103911208 | 7/2014 |
| EP | 0 222 169 | 5/1967 |
| EP | 2 724 625 A1 | 4/2014 |
| FR | 2 273 064 | 12/1975 |
| FR | 2 924 126 A1 | 5/2009 |
| GB | 1 432 039 A | 4/1976 |
| JP | S 4971187 A | 7/1974 |
| JP | S53038653 | 4/1978 |
| JP | 360075244 | 10/1983 |
| JP | H 0568536 A | 3/1993 |
| JP | H 06253770 | 9/1994 |
| JP | 409252707 A | 9/1997 |
| JP | H 11042440 | 2/1999 |
| JP | 2005-179135 | 7/2005 |
| KR | 2012/0064786 A | 6/2012 |
| WO | WO 2010/045368 | 4/2010 |
| WO | WO 2010/120923 A1 | 10/2010 |
| WO | WO 2011/130578 A2 | 10/2011 |
| WO | 2012/109642 A1 | 8/2012 |
| WO | WO 2014/117163 A1 | 7/2014 |
| WO | WO 2015/001261 | 1/2015 |
| WO | WO 2015/007997 | 1/2015 |

OTHER PUBLICATIONS

Molina Grima et al.: "Downstream Processing of cell-mass and products", In: "Handbook of Microalgal Culture: Biotechnology and App Li Ed Phycology", Jan. 1, 2004 (Jan. 1, 2004), Blackwell/Wi Ley, XP008160049, ISBN: 978-0-632-05953-9 pp. 215-251, p. 232.

Anonymous: "Ceramic Grinding Beads", Process Technologies for Tomorrow Jan. 1, 2006 (Jan. 1, 2006), XP055113545, Retrieved from the Internet: URL:http://imperia.mi-verlag.de/imperia/md/upload/product/8r25 hosokawa power beads engl.pdf [retrieved on Apr. 10, 2014] the whole document.

Doucha J et al."Influence of processing parameters on disintegration of Chlorella cells in various types of homogenizers", Applied Microbiology and Biotechnology, vol. 81, No. 3, Aug. 29, 2008 (Aug. 29, 2008), pp. 431-440, XP019654147, Springer, Berlin, DE ISSN: 1432-0614, DOI: 10.1007/500253-008-1660-6 the whole document.

International Search Report, dated Oct. 7, 2014, from corresponding PCT application.

Restriction Requirement, dated Oct. 4, 2017, in U.S. Appl. No. 14/905,686.

Non-Final Rejection, dated Jan. 26, 2018, in U.S. Appl. No. 14/905,686.

Final Rejection, dated Oct. 31, 2018, in U.S. Appl. No. 14/905,686.

Written Opinion of the Searching Authority, dated Oct. 7, 2014, from corresponding International Patent Application No. PCT/FR14/51704, and English Translation.

International Search Report, dated Dec. 10, 2014, from cooresponding International Patent Application No. PCT/FR14/51839, and English Translation.

Written Opinion of the Searching Authority, dated Dec. 10, 2014, from corresponding International Patent Application No. PCT/FR14/51839, and English Translation.

Japanese Patent Application No. JP 2016-522718, English Tranlation of the Notice of Reasons for Rejection, dated Jun. 4, 2018.

Japanese Patent Application No. JP 2016-526681, Notice of Reasons for Rejection, dated Jun. 11, 2018, with English Translation.

Becker, E.W., "Micro-algae as a source of protein," Biotechnology Advances,vol. 25; No. 2, pp. 207-201, (Jan. 26, 2007).

Belasco, Warren, "Algae Burgers for a Hungry World? The Rise and Fall of Chlorella Cuisine," Technology and Culture, 38(3):608-634, (1997).

Chacón-Lee, T.L. and G.E. González-Mariño, "Microalgae for "Healthy" Foods—Possibilities and Challenges", Comprehensive Reviews in Food Science and Food Safety, vol. 9; (Oct. 31, 2010), pp. 655-675.

Krüger, "Kurze Charakteristik einiger niedrerer Organismen im Saftfluss der Laubbaume," Hedwigia, 33: 241-266, (1894). Machine Translation.

Miao et al., "Biodiesel Production From Heterotrophic Microalgal Oil," Biosource Technology, 97(06):841-846, (2006).

Miao et al., "High Yield Bio-Oil Production from Fast Pyrolysis by Metabolic Controlling of Chlorella Protothecoides," J. Biotech., 110:85-93, (2004).

Samarasinghe, Nalin, et al., "Algal Cell Rupture Using High Pressure Homogenization as a Prelude to Oil Extraction." Renewable Energy, vol. 48, (Apr. 20, 2012) pp. 300-308, 2012.

Shi et al., "Production and rapid extraction of lutein and the other lipid-soluble pigments from Chlorella protothecoides grown under heterotrophic and mixotrophic conditions," Nahrung, 43:109-113, (1999).

Shi, et al., "Production of biomass and lutein by Chlorella protothecoides at various glucose concentrations in heterotrophic cultures", Process Biochemistry, 34:341-347, (1999).

Spiden, Erin M. et al., "Critical Analysis of quantitative indicators of cell disruption applied to *Saccharomyces cerevisiae* processed with an industrial high pressure homogenizer", Biochemical Engineering Journal, (Oct. 29, 2012), vol. 70, pp. 120-126, XP055156038, ISSN: 1369-703X, DOI: 10.1016/j.bej.2012.10.008, paragraph [02. 2].

Spiden, Erin M. et al., "Quantitative Evaluation of the Ease of Rupture of Industrially Promising Microalgae by High Pressure Homogenization." Bioresource Technology, vol. 140, pp. 165-171, (Apr. 28, 2013).

Wu et al., "A Comparative Study of Gases Generated from Simulant Thermal Degradation of Autotrophic and Heterotrophic Chlorella," Progress in Natural Science, 2(4):311-318, (1992).

(56) References Cited

OTHER PUBLICATIONS

Wu et al., "Comparative study on Liposoluble Compounds in Autotrophic and Heterotrophic Chlorella Protothecoides," Acta Botanica Sinica, 35(11):849-858, (1992).
Wu et al., "New Discoveries in Study on Hydrocarbons From Thermal Degradation of Heterotrophically Yellowing Algae," Science in China, 37(3):326-35, (Mar. 1, 1994).
Xu, H., et al., "High Quality Biodiesel Production from a Microalgal Chlorella Protothecoides by Heterotrophic Growth in Fermenters." Journal of Biotechnology, vol. 126, pp. 499-507, (2006).
Memorandum Order, *Roquette Frères, S.A.* v. *Solazyme, Inc.*, C.A. No. 14-1442-SLR, District Court for the District of Delaware, Jan. 12, 2016.
Plaintiff and Counter-Defendant Roquette Frères, S.A.'s Reply Brief in Support of Its Motion for Stay Pending Appeal, *Roquette Frères, S.A.* v. *Solazyme, Inc.*, C.A. No. 14-1442-SLR, District Court for the District of Delaware, Jan. 8, 2016.
Defendant and Counterclaimant Solazyme, Inc.'s Brief in Opposition to Plaintiff and Counter-Defendant Roquette Freres, S.A.'S Motion to Stay Pending Appeal, *Roquette Frères, S.A.* v. *Solazyme, Inc.*, C.A. No. 14-1442-SLR, District Court for the District of Delaware, Jan. 6, 2016.
Declaration of Jonathan Wolfson in Support of Defendant and Counterclaimant Solazyme, Inc.'S Opposition to Plaintiff and Counterclaimant Roquette Freres, S.A.'s Motion to Stay Pending Appeal, *Roquette Frères, S.A.* v. *Solazyme, Inc.*, C.A. No. 14-1442-SLR, District Court for the District of Delaware, Jan. 6, 2016, Redacted Public Version.
Declaration of Jeffrey M. Goehring in Support of Plaintiff and Counter-Defendant Roquette Frères, S.A.'s Brief Motion for Stay Pending Appeal, *Roquette Frères, S.A.* v. *Solazyme, Inc.*, C.A. No. 14-1442-SLR, District Court for the District of Delaware, Dec. 28, 2015, Redacted Version Exhibit 1, Basf and Solazyme Launch the First Commercial Microalgae-Derived Betaine Surfactant, Solazyme, Inc., Jul. 28, 2015 Exhibit 2, Solazyme Bunge Renewable Oils Completes Key Redundant Power and Steam Supplies, Solazyme Bunge Renewable Oils, Jun. 30, 2015 Exhibit 3, Solazyme Receives FDA GRAS No Questions Letter for High Oleic Algae Oil, Solazyme, Inc., Feb. 24, 2015 Exhibit 4, Solazyme's (SZYM) CEO Jonathan Wolfson on Q1 2015 Results—Earnings Call Transcript, Solazyme, Inc., May 6, 2015 Exhibit 5, Solazyme's (SZYM) CEO Jonathan Wolfson on Q2 2015 Results—Earnings Call Transcript, Solazyme, Inc., Jul. 30, 2015 Exhibit 6, Solazyme's (SZYM) CEO Jonathan Wolfson on Q4 2014 Results—Earnings Call Transcript, Solazyme, Feb. 26, 2015 Exhibit 7, Redacted in Its Entirety.
Motion to Stay Pending Appeal and Order Granting Motion to Stay Pending Appeal, *Roquette Frères, S.A.* v. *Solazyme, Inc.*, C.A. No. 14-1442-SLR, District Court for the District of Delaware, Dec. 28, 2015.
Memorandum of Law in Support of Motion by Roquette Freres, S.A. for a Stay Pending Appeal, *Roquette Frères, S.A.* v. *Solazyme, Inc.*, C.A. No. 14-1442-SLR, District Court for the District of Delaware, Dec. 28, 2015.
Email dated Nov. 3, 2015, from Gerald Suh of Solazyme, Inc., to Jeffrey M. Goehring of Young & Thompson International Patent & Trademark Law (counsel for Roquette Frères, S.A.).
Letter dated Oct. 6, 2015, from Jeffrey M. Goehring of Young & Thompson International Patent & Trademark Law (counsel for Roquette Frères, S.A.) to Gerald Suh of Solazyme, Inc., and R. James Balls and William E. McShane of Novak Druce Connolly Bove + Quigg LLP (counsel for Solazyme Roquette Nutritionals, LLC), which included the following enclosures: Exhibits 1, 9-12, and 14-15 to the Declaration of Jeffrey M. Goehring in Support of Roquette Frères, S.A.'s Brief in Support of Its Motion for Summary Judgment of Solazyme, Inc.'s Claim for Misappropriation of Trade Secrets, *Roquette Frères, S.A.* v. *Solazyme, Inc.*, C.A. No. 14-01442, District Court for the District of Delaware, D.I. 141, Jun. 22, 2015, Redacted Version Exhibits 2-8 to the Declaration of Jeffrey M. Goehring in Support of Roquette Frères, S.A.'s Brief in Support of Its Motion for Summary Judgment of Solazyme, Inc.'s Claim for Misappropriation of Trade Secrets, *Roquette Frères, S.A.* v. *Solazyme, Inc.*, C.A. No. 14-01442, District Court for the District of Delaware, D.I. 112-1, Jun. 22, 2015 Exhibit 13 to the Declaration of Jeffrey M. Goehring in Support of Roquette Frères, S.A.'s Brief in Support of Its Motion for Summary Judgment of Solazyme, Inc.'s Claim for Misappropriation of Trade Secrets, *Roquette Frères, S.A.* v. *Solazyme, Inc.*, C.A. No. 14-01442, District Court for the District of Delaware, D.I. 112-2, Jun. 22, 2015 Declaration of Jeffrey M. Goehring in Support of Roquette Frères, S.A.'s Brief in Support of Its Motion for Summary Judgment of Solazyme, Inc.'s Claim for Misappropriation of Trade Secrets, *Roquette Frères, S.A.* v. *Solazyme, Inc.*, C.A. No. 14-01442, District Court for the District of Delaware, D.I. 112, Jun. 22, 2015 Roquette Frères, S.A.'s Opening Brief in Support of Its Motion for Summary Judgment of Solazyme, Inc.'s Claim for Misappropriation of Trade Secrets, *Roquette Frères, S.A.* v. *Solazyme, Inc.*, C.A. No. 14-01442, District Court for the District of Delaware, D.I. 140, Jun. 22, 2015, Redacted Version.
Letter dated Nov. 2, 2015, from Jeffrey M. Goehring of Young & Thompson International Patent & Trademark Law (counsel for Roquette Frères, S.A.) to Gerald Suh of Solazyme, Inc., and R. James Balls and William E. McShane of Novak Druce Connolly Bove + Quigg LLP (counsel for Solazyme Roquette Nutritionals, LLC), which included the same enclosures included with the letter dated October 6, 2015.
Email dated Nov. 4, 2015, from Jeffrey M. Goehring of Young & Thompson International Patent & Trademark Law (counsel for Roquette Frères, S.A.) to Gerald Suh of Solazyme, Inc., and R. James Balls and William E. McShane of Novak Druce Connolly Bove + Quigg LLP (counsel for Solazyme Roquette Nutritionals, LLC).
Opinion dated Dec. 21, 2015 in *Roquette Frères, S.A.,* v. *Solazyme, Inc.*, Case No. 1:14-cv-01442 (D. Del. 2015) granting Solazyme's motion for an order confirming the arbitration award rendered by CPR International Institute for Conflict Prevention & Resolution on Feb. 19, 2015, in favor of Solazyme, Inc.
Youzhi Jiagong, (Jun. 8, 2007), "Oil Processing Technology (2nd edition)", Chemical Industry Press, Title Page, Publication Page, Table of Contents, pp. 206-213, (in Chinese).
"Linoleic acid and α-linolenic acid are real essential fatty acids", (Mar. 1998), Title Page, Publication Page, Table of Contents, Chapter 2: Essential Fatty Acids (pp. 12-13) and Chapter 15: Selection of the most suitable fatty acids (pp. 89-91), with English translation.
Bowman, Barbara A. and Robert M. Russell (eds.), "Present Knowledge in Nutrition" (1st Edition), (Oct. 2004), Title page, Publication Page, Table of Contents, p. 231 (in Chinese).
"Auxenochlorella", article from Wikipedia, Retrieved from the Internet on Mar. 23, 2016, "https://en.wikipedia.org/w/index.php?title=Auxenochlorella&oldid=711518993".
Clore, G.M. and E.M. Chance, A computer analysis of cyanide stimulated oxygen uptake in *Chlorella protothecoides.* (Jul. 1977) FEBS Lett. 79 (2):353-356.
"Algen—Nudein ais Altmark Spezialitat (Algae noodles: a specialty from Altmark region)" in German language, and other *Chlorella* Food products, (Oct. 9, 2007), 3 pages.
Imai, Ichiro, et al. "Advanced research on Shellfish poisonings: Current Status and overview", Table of Contents, Chapters 1 and Chapter 4, 11 pages.
"Aoko's toxin", Aichi Prefectural Institute of Public Health, 6 pages. [Retrieved from the Internet Oct. 13, 2016: <URL: http://www.pref.aichi.jp/eiseiken/5f/bloom_t.html].
Lee, Yuan-Kun, "Commercial Production of microalgae in the Asia-Pacific rim", Journal of Applied Phycology, 9:403-411, (Oct. 29, 1997).
Kay, Robert A., "Microalgae as Food and Supplement", Critical Reviews in Food Science and Nutrition, 30(6):555-573 (Feb. 1991).
Usuki, Riichiro and Luniko Kamata,"Experimental Trials on the Role of Lipids in Good Taste and Good Body of Foods", Research reports of Shokei Gakuin College 53, May 2006, p. 85-90 (in Japanese with English Abstract).
"Chlorella Photosynthesis—Dictionary", last modified Mar. 23, 2015, Retrevied from the Internet: <URL: (http://photosyn.jp/pwiki/

(56) References Cited

OTHER PUBLICATIONS index.php?%E3%82%AF%E3%83%AD%E3%83%AC%E3%83%A9) with English Machine Translation.

Hirashima, Ryuta, "Framework of evaluation on inventive step requirement and significance of 'technical problem'", Patent 2010, 63(5): 34-49 (in Japanese; no translation).

Ullmann, Jorg, "The Difference between *Chlorella* vulgaris and *Chlorella pyrenoidosa*", (2006) (http://www.algomed.de/index.php?op=algenfarm_geschichte).

"History of the algae farm: Chlorella Algae—Roquette Klötze GmbH", [Retrieved from the Internet Nov. 25, 2016: <URL: (http://www.algomed.de/index.php?op=algenfarm_geschichte)].

Kirk, J. et al., "Mastitis Control Program for Prototheca Mastitis in Dairy Cows", 6 pages. <<URL: milkquality.wisc.edu/wp=content/uploads/2011/09/mastitis-control-program_prototheca-mastitis.pdf>>.

Oral Summary, dated Nov. 7, 2016, for Invalidation Hearing for Japanese Patent No. 5731982 (in Japanese).

Oral Summary by the Patentee, dated Nov. 29, 2016, for Invalidation Hearing for Japanese Patent No. 5731982 (in Japanese).

USDA National Nutrient Database (https://ndb.nal.usda.gov/ndb/).

Environmental Stresses in Non Mammalian Organisms, p. 29. with English translation.

Letter from Ray Matulka to Paulette Gaynor and Sylvester Mosley, dated Apr. 18, 2013, re: Request to Cease Evaluation of GRN 000450, Letter from Ray Matulka to Paulette Gaynor, dated Apr. 18, 2013, re: High Lipid Chlorella protothecoides S106 Flour GRAS Notification and GRAS Exemption Claim (dated Apr. 18, 2013).

Solazyme Market and Products, (2005).

Letter from Susan Cho to Susan Carlson, dated Jul. 25, 2011 and "RF1's Chlorella vulgaris GRAS Self affirmation (dated Jul. 16, 2010)."

[Retrieved from the Internet Oct. 13, 2016: <URL: http://hfnet.nih.go.jp/contents/detail105.htm] (in Chinese).

"Roquette Freres, S.A. and Solazyme, Inc. Agree to Dissolve Microalgae Join Venture", (Jun. 24, 2013) Press Release, Lestrem, France.

Standard Tables of Food Composition in Japan 2015 (Seventh Revised Edition), Table of Fatty Acid Composition, Edited by The Council for Science and Technology, the Ministry of Education, Culture, Sports, Science and Technology, (available from http://www.mext.gojp/a_menu/syokuhinseibun/1365295.htm) [Retrieved from the Internet Oct. 12, 2016: <URL: (http://www.algomed.de/index.php?op=algenfarm_geschichte)]http://www.geocities.jp/jr2bvb/syokuhin/sibousan/oil_s.htm].

"'Taste' of Lipids?" [Retrieved from the Internet Oct. 12, 2016: <URL: (https://sites.google.com/site/coffeetambe/coffeescience/physiology/taste/fat] with English Machine Translation.

Japanese Laid-Open Publication No. 2000-175680 (translator's note: an English language member of the same patent family: EP 1142985 (A1)).

Japanese Laid-Open Publication No. 2002-223787 (translator's note: no English language counterpart could be located).

http://mcc.nies.go.jp/strainList.do?strainId=2555&condition=Auxenochlorella+protothecoides.

http://mcc.nies.go.jp/strainList.do?strainId=2568&condition=Auxenochlorella+protothecoides.

*Roquette Freres S.A.* v. *Solazyme Inc.*, Delaware District Court, Case No. 1:14-cv-01442 District Judge Sue L. Robinson, presiding, Solazyme, Inc.'s Answer to Plaintiff Roquette Freres, S.A.'S Complaint, Petition to Confirm Arbitration Award and Counterclaims, filed Feb. 26, 2015, 29 pages.

Joint Venture and Operating agreement of Solazyme Roquette Nutritionals, LLC., copy dated Nov. 7, 2015.

*Solazyme, Inc.* vs. *Roquette Freres*, S.A., Arbitration Award, dated Feb. 19, 2015.

Request for Invalidation, dated Jan. 7, 2015, for Chinese Patent Application No. 200980149978.1, 21 pages (in Chinese).

Supplemental Statement for Request for Invalidation, dated Dec. 2, 2015, for Chinese Patent Application No. 200980149978.1, 35 pages (in Chinese), including the list of submitted Counter Evidences on p. 1-2.

Notification of Acceptance of Request for Invalidation, dated Jan. 28, 2016, for Chinese Patent Application No. 200980149978.1, 4 pages (in Chinese).

Documents filed by the Petitioner—Part II, dated Apr. 29, 2015, for Chinese Patent Application No. 200980149978.1, 21 pages (in Chinese), including : Jia, Xuan, et al., "Removal of Total nitrogen form wastewater discharge from a chemical pertilizer plant by Chlorella protothecoides USTB-01", Chinese Journal of Environmental Engineering, (Apr. 2010), 4(4):737-740 (in Chinese).

Documents filed by the Petitioner—Part III, dated May 5, 2015, for Chinese Patent Application No. 200980149978.1, 21 pages (in Chinese), including :, including : Singelton Paul and Diana Sainsbury, "Dictionary of Microbiological and Molecular Biology, (3rd Ed. 2006)", pp. 155 (and Chinese translation thereof) Singelton Paul and Diana Sainsbury, "Dictionary of Microbiological and Molecular Biology, (2nd Ed. 1987)", pp. 178-179 (and Chinese translation thereof).

Statement of Grounds & Particulars of Opposition, Grounds for Opposition, in the matter of Australian Patent Application No. 2009303354 in the name of Solazyme, Inc. and Opposition by *Roquette Frères, S.A.* v. *Solazyme, Inc.*, Commonwealth of Australia Mar. 3, 2016, (21 pages).

Declaration of Michael Armin Borowitzka in the matter of Australian Patent Application No. 2009303354 in the name of Solazyme, Inc. and Opposition by *Roquette Frères, S.A.* v. *Solazyme, Inc.*, Commonwealth of Australia Jun. 2, 2016, (32 pages).

Exhibit MB-1, Federal Court of Australia, Practice Note CM7, Expert Witnesses in Proceedings on the Federal Court of Australia, commenes June 4, 2013 Exhibit MB-2, Michael Armin Borowitzka Curriculum Vitae Exhibit MB-3, J. M. Hundley, R. B. Ing and R. W. Krauss, "Algae as Sources of Lysine and Threonine in Supplementing Wheat and Bread Diets", Science, New Series, vol. 124, No. 3221 (Sep. 21, 1956), pp. 536-537. Exhibit MB-4, Krauss, Robert W., "Mass Culture of Algae for Food and Other Organic Compounds," American Journal of Botany, vol. 49, No. 4 (Apr. 1962), pp. 425-435. Exhibit MB-5, Lee, Yuan-Kun, "Commercial Production of microalgae in the Asia-Pacific rim", Journal of Applied Phycology, 9:403-411, (Oct. 29, 1997) Exhibit MB-6, Soong, Pinnan, "Productions and Development of *Chlorella* and *Spirulina* in Taiwan", *Algae Biomass: Production and Use*, Gedaliah Shelef and Carl J. Soeder (eds.), North-Holland Biomedical Press, (Dec. 1980), pp. 97-113 and title and copyright page. Exhibit MB-7, Kawaguchi, Kotaro, "Microalgae Production Systems in Asia", *Algae Biomass: Production and Use*, Gedaliah Shelef and Carl J. Soeder (eds.), North-Holland Biomedical Press, (Dec. 1980), pp. 25-33 and title and copyright page. Exhibit MB-8, Kay, Robert A., "Microalgae as Food and Supplement", Critical Reviews in Food Science and Nutrition, 30(6):555-573 (Feb. 1991). Exhibit MB-9, Raymundo et al., "Fat mimetic capacity of *Chlorella vulgaris* biomass in oil-in-water food emulsions stabilized by pea protein," Food Research International, 38:961-965, (Feb. 25, 2005). Exhibit MB-10, Samejima, H. and J Myers, "On the Heterotrophic Growth of *Chlorella pyrenoidosa*", J. Gen Microbiol, (1958), 18:107-117.

Exhibit MB-11, Aoki, Shigeji and Eiji Hase, "De- and Re-Generation of Chloroplasts in the Cells of Chlorella Protothecoides", Plant & Cell Physiol, (Sep. 5, 1964), vol. 5, pp. 473-484 [Retrieved from the internet on Jun. 7, 2013 from http://pcp.oxfordjournals.org/ by Reprints Desk ]. Exhibit MB-12, Becker, E.W., "Micro-algae as a source of protein," Biotechnology Advances, 25:207-201, (Mar.-Apr. 2007). Exhibit MB-13, Iwamoto, Hiroaki, "Industrial Production of Microalgal Cell-mass and Secondary Products—Major Industrial Species Chlorella", Chapter 11, Handbook of Microalgal Culture: Biotechnology and Applied Phycology, Amos Richmond (eds), (Dec. 1, 2003), pp. 255-263. Exhibit MB-14, Petkov et al., "Which are fatty acids of the green alga Chlorella?," Biochemical Systematics and Ecology, 35:281-285, (2007). Exhibit MB-15, Gladu, Patricia K., et al. "Sterol, Fatty Acid and Pigment Characteristics of UTEX 2341, a Marine Eustigmatophyte Identified Preivously as Chlorella Minutissuma (Chlorophyceae)" J. Phycol., (Jun. 21,

(56) References Cited

OTHER PUBLICATIONS

1995), 31:774-777. Exhibit MB-16, Xu et al., "High Quality Biodiesel Production From a Microalga Chlorella Protothecoides by Heterotrophic Growth in Fermenters," Journal of Biotechnology, 126(4):499-507, (May 2006). Exhibit MB-17, Matsuka et al., "Changes in Contents of Carbohydrate and Fatty Acid in the Cells of Chlorella Protothecoidesduring the process of De- and Re-Generation of Chloroplasts," Plant and Cell Physiol., 7:651-662 (Sep. 24, 1966). Exhibit MB-18, Xuan, J. et al., "Removal of total nitrogen from wastewater discharge from a chemical fertilizer plant by Chlorela protothecoides USTB-01", Chinese Journal of Environmental Engineering, (Apr. 2010), vol. 4, No. 4, pp. 737-740.
Exhibit MB-19, Australian Application No. 2009303354B2 from International Patent Application No. PCT/US2009/060692, naming Solazyme, Inc., International Patent Publication No. 2010/045368, dated Apr. 22, 2010. Exhibit MB-20, Pabst, W., "Nutritional evaluation of nonsewage microalgae by the rat balance method," Arch. HyrobioL Beih, (Dec. 1978), pp. 65-70 Exhibit MB-21, Urano, et al., "Effect of Osmotic Stabilizers on Protoplast Generation on Chlorella ellipsoidea Yellow/White Color Mutants", Journal of Bioscience and Bioengineering, vol. 90, No. 5, 567-569, (2000). Exhibit MB-22, Kamiya, "Effects of Blue Light and Ammonia on Nitrogen Metabolism in a Colorless Mutant of Chlorella", Plant Cell Phyiol., 30(4):513-521 (1989) Exhibit MB-23, Biello et al., "Biofuel of the Future: Oil from Algae," Scientific American, 2 pages, (Jan. 9, 2008).
Evidence in Support, In the matter of Australian Patent Application No. 2009303354 in the name of Solazyme, Inc. and Opposition by *Roquette Frères, S.A.* v. *Solazyme, Inc.*, Commonwealth of Australia, Jun. 3, 2016, (1 page).
Declaration of Young J. Suh in the matter of Australian Patent Application No. 2009303354 in the name of Solazyme, Inc. and Opposition by *Roquette Frères, S.A.* v. *Solazyme, Inc.*, Commonwealth of Australia, Aug. 31, 2016, (94 pages) Exhibit YS1, Arbitration Award, Solazyme Inc. vs. Roquette Frères, Case 1:14-cv-O1442-SLR, Document 153, Filed Dec. 21, 2015 Exhibit YS2, French Patent Publication No. FR 2 924 126, filed Nov. 28, 2007. Exhibit YS3, Memorandum Opinion, Document 153, *Roquette Frères, S.A.* vs. *Solazyme Inc.*, Case 1:14-cv-O1442-SLR, filed Dec. 21, 2015.
Declaration of Craig Patch in the matter of Australian Patent Application No. 2009303354 in the name of Solazyme, Inc. and Opposition by *Roquette Frères, S.A.* v. *Solazyme, Inc.*, Commonwealth of Australia, Sep. 5, 2016, (22 pages) Exhibit CP-1, Federal Court of Australia, Practice Note CM7, Expert Witnesses in Proceedings on the Federal Court of Australia, commences Jun. 4, 2013. Exhibit CP-2, Craig Patch Curriculum Vitae.
Declaration of Craig Patch in the matter of Australian Patent Application No. 2009303354 in the name of Solazyme, Inc. and Opposition by *Roquette Frères, S.A.* v. *Solazyme, Inc.*, Commonwealth of Australia, Sep. 28, 2016, (42 pages). Exhibit CP3, Record of Views Formed in Response to Inquires, updated Mar. 2015 (20 pages) Exhibit CP4, Huss, V.A.R., et al., "Biochemical Taxonomy and Molecular Phylogeny of the Genus *Chlorella* Sensu Lato (Chlorophyta)1", J. Phycol. 35, 587-598 (Jan. 15, 1999).
Evidence in Answer, in the matter of Australian Patent Application No. 2009303354 in the name of Solazyme, Inc. and Opposition by *Roquette Freres, S.A.* v. *Solazyme, Inc.*, Commonwealth of Australia, Sep. 29, 2016, (1 page).
Declaration of Michael Armin Borowitzka in the matter of Australian Patent Application No. 2009303354 in the name of Solazyme, Inc. and Opposition by *Roquette Frères, S.A.* v. *Solazyme, Inc.*, Commonwealth of Australia, Dec. 21, 2016, (14 pages).
Evidence in Reply, in the matter of Australian Patent Application No. 2009303354 in the name of Solazyme, Inc. and Opposition by *Roquette Frères, S.A.* v. *Solazyme, Inc.*, Commonwealth of Australia Dec. 23, 2016, (1 page).
"Roquette's Microalgae High Lipid Algal Flour Wins Most Innovative Food Ingredient at the 2013 Fi Europe Excellence Award," www.PRnewswire.com/news-release/roquettes-migroalgae-high-lipid-algal-flour-wins-most-innovative-food-ingrediant-at-the-2013-fi-europe-excellence-awards, (Nov. 25, 2013), pp. 1-5.
Freshwater Algae Culture Collection at the Institute of Hydrobiology (FACHB-collection), certification letter by the Chinse Academy of Science, "Chlorella vulgaris", (No Date).
Zhou, Lian-ning et al. "Effects of Environmental Factors on Nitrogen and Phosphorus Removal by *Chlorella vulgaris* in Wastewater", Current Biotechnology, (Jan. 25, 2015), vol. 5, No. 1, Title page, Publication Page, Table of Contents (I Chinese and English), pp. 60-65, with English abstract.
Evidence 1, Explanation paper, filed with IP High Court Case No. H29 (gyo-ke) 10149 on Oct. 6, 2017 in Invalidation Appeal No. 2016-800012 against Japanese Patent No. 5731982, with English translation.
First Statement, Substantive Brief, filed with IP High Court Case No. H29 (gyo-ke) 10149 on Nov. 17 2017 in Invalidation Appeal No. 2016-800012 against Japanese Patent No. 5731982, with English translation.
Second Statement, Substantive Brief, filed with IP High Court Case No. H29 (gyo-ke) 10149 on Jan. 17, 2018 in Invalidation Appeal No. 2016-800012 against Japanese Patent No. 5731982. With Explanation Paper for the Evidence. Japanese Only.
Opponent's Outline of Submissions, in the Matter of Australian Patent Application No. 2009303354 in the name of Corbion Biotech, Inc., dated Jan. 24, 2018, 48 pages.
Response to Reg 5.23 Request, in the Matter of Australian Patent Application No. 2009303354 in the name of Corbion Biotech, Inc., filed Feb. 5, 2018, 18 pages. Letter from David Sieveking, dated Jan. 24, 2018 Statutory Declaration of Dr. Daniel Peter Sieveking, dated Jan. 24, 2018. Exhibit DS-1, Kyle, David, "Production and Use of Lipids from Microalgae", Microalgal Lipids, Lipid Technology, (May-Jun. 1992), pp. 59-64. Exhibit DK-2, Chen et al., "High cell density culture of microalgae in heterotrophic growth," Trends in Biotechnology, 14:421-426, (1996).
Consent to Withdraw, dated Feb. 14, 2018, for IP High Court Case No. H29 (gyo-ke) 10149, Invalidation Appeal No. 2016-800012, against Japanese Patent No. 5,731,982, in the names of TerraVia Holdings, Inc. in Japanese Only, [SOLA0043JP-0807X01JP].
Request for Withdrawal of Opposition, by Roquette Freres, to Grant of Australian Patent Application No. 2009303354, in the Name of Corbion Biotech, Inc., dated Mar. 13, 2018.
Opposition Proceedings, dated Mar. 14, 2018, Acknowledgement of the the Request for Withdrawal of Opposition, by Roquette Freres, to Grant of Australian Patent Application No. 2009303354.
Third Party Observations from Roquette Freres, dated Aug. 31, 2017, for Chinese patent for invention No. 200980149978.1 (in Japanese with English Translation).
Third Party Observations from Roquette Freres, dated Aug. 31, 2017, for Chinese patent for invention No. 201080026237.7 (in Japanese with English Translation).
"Enter the World of Microalgae," Roquette (Jun. 2014).

* cited by examiner

OPTIMISED METHOD FOR BREAKING CHLORELLA WALLS BY MECHANICAL CRUSHING

The present invention relates to an optimized process for breaking the cell walls of microalgae of the *Chlorella* genus, more particularly *Chlorella vulgaris, Chlorella sorokiniana* or *Chlorella prototheicoides* on an industrial scale.

PRESENTATION OF THE PRIOR ART

It is well known to those skilled in the art that chlorellae are a potential source of food, since they are rich in proteins and other essential nutrients.

They contain in particular 45% of proteins, 20% of fats, 20% of carbohydrates, 5% of fibers and 10% of minerals and vitamins.

In order to efficiently use *Chlorella* in food, use is often made of "cell breaking" so as to facilitate its digestibility and its absorption rate.

This "cell breaking" of the microalgae is well described in the patent and non-patent literature through the use of varied technologies:
- physical technologies (ultrasound, microbeads, heat shocks, high pressure, etc.)
- chemical technologies (acids, alkalis, hydrophilic organic solvents, etc.)
- enzymatic technologies (cellulase, lipase, etc.).

These technologies are, for example, described in patent applications or patents KR 2012/0064786, CN 101756300, JPH 0568536, JPS 4971187 or U.S. Pat. No. 5,330,913 or in scientific articles such as those by Sander & Murthy, 2009, in *ANASABE Annual International Meeting*, or Zheng et al., 2011, in *Applied Biochemistry*, 164, 7, 1215-1224.

However, it is generally lamented that these various mechanical, chemical or enzymatic approaches cannot be very successfully extrapolated to an industrial scale.

The difficulties are in fact considerable when it is necessary to process microalgal biomasses:
- which have a high cell density (>100 g/l), and/or
- the cell wall of which has a particularly high mechanical strength.

This is the case for the vast majority of microalgae of the *Chlorella* genus.

The technological choice of the cell-breaking methods becomes even more limited when, added to the difficulties associated with the physiology of the microalgae, there are industrial constraints of the type:
- high production capacity,
- reliability,
- operating costs,
- investment costs, etc.

Finally, on an industrial scale, those skilled in the art favor mechanical milling technologies to the detriment of chemical and enzymatic approaches, more particularly with two options:
- milling using microbeads, or
- high-pressure rupture technology.

Be that as it may, the milling of microorganisms requires a significant energy input and therefore has a not insignificant impact on cost price.

This is particularly true with regard to microalgae of *Chlorella* type which have a very strong wall.

"Bead Mill" (horizontal bead mill) technology constitutes a technological choice capable of satisfying these various problems.

However, its impact with respect to:
- capital expenditures, in particular in terms of development costs and non-consumable item costs (acronym "CAPEX") and
- operating expenses, in particular energy expenses (acronym "OPEX"), is significant and requires optimization in order to improve facility performance levels.

All these constraints, both technological and financial, constitute a curb on development of this "Bead Mill" technology on an industrial scale.

SUBJECT OF THE INVENTION

In order to overcome these constraints, the applicant company chose to carry out its work on controlling the bead-milling technology in order to manage to optimize the energy costs (OPEX) and also the investment capacity required in order to achieve this (CAPEX).

To do this, the applicant company chose to carry out a study to evaluate, on a laboratory scale, the impact of the key parameters in carrying out this bead-milling technology, said key parameters conditioning, on an industrial scale, the optimization of the OPEX and CAPEX.

These key parameters are:
- the bead density,
- the bead diameter,
- the filling rate of the milling chamber,
- the pass mode,
- the peripheral speed of the milling disks,
- the cell concentration.

This work led the applicant company to provide a process for the mechanical milling, on an industrial scale, of cells of microalgae of the *Chlorella* genus, the mechanical milling being carried out in a system of horizontal bead mill type, characterized in that:
- the beads have an apparent density of between 2 and 3.5 kg/l, and
- the filling rate of the milling chamber is greater than or equal to 80%.

Preferably, the microalgae of the *Chlorella* genus are chosen from the group consisting of *Chlorella vulgaris, Chlorella sorokiniana* and *Chlorella prototheicoides*, and are more particularly *Chlorella prototheicoides*.

Preferentially, the process in accordance with the invention comprises:
- the use of zirconium silicate beads, and/or
- a filling rate greater than or equal to 85%.

A first embodiment of the process in accordance with the invention comprises carrying out the milling in continuous mode by means of a series of successive passes.

A second embodiment of the process in accordance with the invention comprises the use of beads having a diameter of less than 1 mm, preferably less than 0.8 mm.

The applicant company has moreover found that a particular combination of the parameters for carrying out the mechanical milling of microalgae of the *Chlorella* genus, in particular *Chlorella prototheicoides*, can make it possible to optimize the OPEX to the detriment of the CAPEX, and vice versa.

The applicant company thus offers variants of its process in accordance with the invention which allow those skilled in the art to choose their configuration in comparison with their specifications (gain in terms of energy of consumption or of cost of investment in equipment).

Thus, in order to optimize the OPEX, the applicant company has found that a first variant may be to moderate the density of the microalgae to be milled, to a level for example of less than 250 g/l.

A second variant may be the choice of a moderate peripheral speed of the milling disks, for example less than 10 m/s.

These two variants are not mutually exclusive. The process may exhibit these two variants or one of the two.

In order to optimize the CAPEX, the applicant company has found that it is necessary, conversely, to increase the cell density of the microalgae to be milled, to a level for example of greater than 250 g/l.

A second variant may be the choice of an accentuated peripheral speed of the milling disks, for example greater than 10 m/s.

Here again, these two variants are not mutually exclusive. The process may exhibit these two variants or one of the two.

DETAILED DESCRIPTION OF THE INVENTION

The applicant company has found that the managed exploitation of the mechanical milling technology to break the wall of microalgae of the *Chlorella* genus, using a horizontal bead mill, makes it possible to achieve a desired degree of milling while optimizing the energy costs (OPEX) and investment costs (CAPEX).

The improvement in the overall performance level of the facility is thus based on the choice of precise parameters which make it possible to optimize the OPEX and CAPEX or to find the best compromise.

The process, in accordance with the invention, for the mechanical milling, on an industrial scale, of cells of microalgae of the *Chlorella* genus, the mechanical milling being carried out in a system of horizontal bead mill type, is therefore characterized in that:
  the beads have an apparent density of between 2 and 3.5 kg/l, and
  the filling rate of the milling chamber is greater than or equal to 80%.

Apparent Density of the Beads

As will be exemplified hereinafter, the zirconium silicate beads exhibit the best performance levels for this application by limiting the specific energy required to achieve the targeted degree of milling. Thus, the apparent density is between 2 and 3.5 kg/l, preferably between 2 and 3.2 kg/l.

Filling Rate

The filling rate is defined as being the empty volume of the milling chamber minus the volume occupied by the stirring system (generally defined by the supplier).

The specific energy at lower filling rate is slightly higher than at high filling rate. Furthermore, the productivity therein is improved.

Consequently, the process in accordance with the invention preferentially comprises:
  the use of zirconium silicate beads, and/or
  a filling rate greater than or equal to 85%.

Preferably, the process uses zirconium silicate beads and a filling rate greater than 85%.

The filling rate may be between 80% and 95%, in particular between 85% and 90%.

A first embodiment of the process in accordance with the invention comprises carrying out the milling in continuous mode by means of a series of successive passes.

The bead-milling operation is conventionally carried out according to several operating schemes: recirculation, single pass, multiple passes, etc.

In one industrial configuration, a continuous system is preferred and involves a single-pass or multiple-pass operating mode.

As will be exemplified hereinafter, the performance level is improved by increasing the number of passes since a higher degree of milling is obtained at equivalent residence time and without a significant increase in the specific energy.

In the process in accordance with the invention, a multiple-pass mode (several mills in series) will be preferred for the optimization of the process on an industrial scale. In particular, the process may comprise 2, 3, 4, 5 passes or more.

A second embodiment of the process in accordance with the invention comprises the use of beads having a diameter of less than 1 mm, preferably less than 0.8 mm. In one particular embodiment, the beads have a diameter of between 0.3 and 0.8 mm.

The impact of the diameter of the milling beads is studied on the same zirconium silicate range (beads of the same density) with a diameter ranging from 0.3 mm to 1.7 mm.

As will be exemplified hereinafter, the beads of small diameter allow a better energy performance level and also a better productivity.

In order to enable those skilled in the art to choose their configuration in comparison with their specifications (sees favoring the OPEX or the CAPEX), the applicant company offers variants of its process in accordance with the invention.

The applicant company has found that these options can be provided by adjusting:
  the cell density of the microalgae of the *Chlorella* genus to be milled,
  the peripheral speed of the milling disks.

Cell Density

The impact of the cell concentration of the biomass on the milling performance levels is evaluated by choosing a biomass from the same production batch, prepared at several concentrations (20%, 25.2% and 32.9%).

The milling is carried out under the same conditions and the results are compared relative to the solids content of the samples thus generated.

The results are interpreted from two different angles:
  by analyzing the impact of the cell concentration on the specific milling energy required to obtain a defined degree of milling,
  by analyzing from the productivity angle, the flow rate of introduction of the biomass (relative to the dry biomass) in comparison with the targeted degree of milling.

Peripheral Speed of the Milling Disks

The optimization of the milling also requires the optimal peripheral speed of the milling disks to be defined.

The results are also interpreted from two different angles:
  by analyzing the specific milling energy as a function of the peripheral speed,
  by analyzing from the productivity angle, according to the peripheral speed, the flow rate required to achieve the targeted degree of milling.

Moreover, problems of abrasion of the milling disks and chamber and also bead-wear problems are to be considered since they may have a not insignificant economic impact on the process.

The applicant company therefore recommends limiting the peripheral speed to a value of less than 15 m/s (or even 13 m/s) in order to avoid excessive abrasion.

Thus, in the case of the milling of a *Chlorella*, in particular of *Chlorella protothecoides* type, to optimize the OPEX, the applicant company has found that a first variant may be:
- to moderate the density of the microalgae to be milled to a level of less than 250 g/l and/or
- to choose a peripheral speed of the milling disks of less than 10 m/s.

Preferably, the density of the microalgae to be milled is greater than or equal to 150 g/l and less than 250 g/l. Preferably, the peripheral speed of the milling disks is greater than or equal to 6 m/s and less than 10 m/s.

To optimize the CAPEX, in the case of the milling of a *Chlorella*, in particular of *Chlorella protothecoides* type, the applicant company has found that it is necessary, conversely:
- to increase the cell density of the microalgae to be milled to a level of greater than 250 g/l and/or
- to choose a peripheral speed of the milling disks of greater than 10 m/s.

Preferably, the density of the microalgae to be milled is greater than 550 g/l and less than or equal to 350 g/l. In particular, the peripheral speed of the milling disks may be between 10 m/s and 15 m/s, preferably between 11 m/s and 13 m/s.

Of course, the present invention relates to any combination of embodiments described in the present application.

The term "industrial scale" is preferably intended to mean a process in which:
- the volume of the milling chamber is greater than or equal to 100 liters, preferably greater than or equal to 500 liters; and/or
- the flow rate is greater than 1 $m^3$/h; and/or
- a batch is from 1 to 200 $m^3$.

The invention will be understood more clearly from the examples which follow, which are intended to be illustrative and nonlimiting.

EXAMPLES

Example 1

**Preparation of a Biomass of *Chlorella protothecoides* Microalgae and Presentation of the Tools Used**

The fermentation protocol is adapted from the one described entirely generally in patent application WO 2010/120923.

The production fermenter is inoculated with a pre-culture of *Chlorella protothecoides*. The volume after inoculation reaches 9000 l.

The carbon source used is a 55% w/w glucose syrup sterilized by application of a time/temperature scheme.

The fermentation is a fed-batch fermentation during which the glucose flow rate is adjusted so as to maintain a residual glucose concentration of from 3 to 10 g/l.

The production fermenter time is from 4 to 5 days.

At the end of fermentation, the cell concentration reaches 185 g/l.

During the glucose feed phase, the nitrogen content in the culture medium is limited so as to allow the accumulation of lipids in an amount of 50% (by weight of biomass).

The fermentation temperature is maintained at 28° C.

The fermentation pH before inoculation is adjusted to 6.8 and is then regulated on this same value during the fermentation.

The dissolved oxygen is maintained at a minimum of 30% by controlling the aeration, the counter pressure and the stirring of the fermenter.

The fermentation must is heat-treated over an HTST zone with a scheme of 1 min at 75° C. and cooled to 6° C.

The biomass is then washed with decarbonated drinking water with a dilution ratio of 6 to 1 (water/must) and concentrated to 250 g/l (25% DCW "Dry Cell Weight") by centrifugation using an Alfa Laval Feux 510.

Bead-Milling Technology

The fermentation biomass thus prepared is used to carry out a screening of the milling parameters on a laboratory bead mill:

| Machine Type | LabStar LS1 |
|---|---|
| Equipment | LME |
| Chamber volume (liter) | 0.7 |
| Peripheral speed (m/s) | 8 to 12 |
| Feed flow rate (kg/h) | 10 to 90 |
| Bead material | Glass |
| | Zirconium Silicate |
| | Zirconium Oxide |
| Bead diameter (mm) | 0.3 to 1.7 |
| Filling rate (%) | 80 to 90% |

The results of the parameters studied are characterized by several points obtained using several successive passes at constant flow rate.

The curves thus obtained for each series of parameters tested are then compared relative to one another in terms of specific energy or of productivity.

Moreover, for the study of a specific parameter, the biomass used for the test comes from the same batch in order to dispense with the composition variability from one batch to another.

Measurement of the Degree of Cell Breaking:

The degree of milling is measured by microscopic counting of the residual cells after milling, relative to the initial reference sample.

The samples are diluted to 1/800. The analysis is carried out by counting on a Malassez cell according to the standard method of use under an optical microscope at a magnification of 10×40.

The degree of cell breaking is determined by calculating the percentage of residual cells relative to the initial reference sample.

Example 2

Optimization of the Milling Parameters Bead Density

The impact of the density of the milling beads is studied using a selection of beads made of materials having different densities but the same diameter (0.6 mm):

| | Beads | | |
|---|---|---|---|
| | Glass | ZS (Zirconium Silicate) | ZO (Zirconium Oxide) |
| Density (kg/l) | 2.5 | 4 | 6 |

-continued

| | Beads | | |
|---|---|---|---|
| | Glass | ZS (Zirconium Silicate) | ZO (Zirconium Oxide) |
| Apparent density (kg/l) | 1.5 | 2.5 | 3.6 |
| Chemical composition | $SiO_2$ (%) 72.5<br>$Na_2O$ (%) 13<br>CaO (%) 9<br>MgO (%) 4 | $ZrO_2$ (%) 55-65<br>$SiO_2$ (%) 35-40 | $ZrO_2$ + $HfO_2$ (%) 95<br>$Y_2O_3$ (%) 5 |

The comparison of the results obtained, presented in FIG. 1, at equivalent degree of milling according to the material of the beads used under the same operating conditions, demonstrates a significant difference in the specific energy consumed.

The beads of high density (ZO—zirconium oxide) cause a much higher specific energy consumption than the zirconium silicate beads.

Although the glass beads have a lower density, the performance levels obtained are not as good, thereby requiring a higher number of passes to achieve the targeted degree of milling, generating a higher specific energy consumption.

The zirconium silicate beads exhibit the best performance levels for this application by limiting the specific energy required to achieve the targeted degree of milling.

Bead Diameter

The impact of the diameter of the milling beads is studied on the same zirconium silicate range (beads of the same density) with a diameter ranging from 0.3 mm to 1.7 mm.

The results obtained, presented in FIG. 2, under the same operating conditions while varying only the bead diameter, demonstrate a strong impact of this parameter on the milling performance levels.

With a large diameter (in this case 1.7 mm), the number of passes and also the specific energy required to achieve the targeted degree of milling is significantly higher than with a small diameter.

The difference between the 0.3 mm and 0.6 mm beads is less significant. The beads of small diameter allow a better energy performance level and also a better productivity.

Chamber Filling Rate

As shown in FIG. 3, the specific energy at low filling rate is slightly higher than when the filling rate is high.

Furthermore, the productivity therein is improved (under the same operating conditions, the degree of milling obtained at the 1st and 2nd pass is higher at a filling rate of 90% than at a filling rate of 80%).

Operating Scheme—Impact of the Pass Mode

As shown in FIG. 4, in terms of residence time in the milling chamber, the three operating schemes tested (single pass, multiple passes) are equivalent (1 pass at 30 kg/h/2 passes at 60 kg/h/3 passes at 90 kg/h).

Moreover, the specific milling energy is almost equivalent to these three schemes.

However, the performance level is improved by increasing the number of passes since a higher degree of milling is obtained at equivalent residence time and without a significant increase in the specific energy.

A multiple-pass mode (several mills in series) will therefore be preferred for the optimization of the process on an industrial scale.

Peripheral Speed of the Milling Disks

According to FIG. 5: By analyzing relatively the specific milling energy as a function of the peripheral speed, the relative position of the curves with respect to one another demonstrates that, at a defined degree of milling, operation at a high peripheral speed requires a significantly higher specific energy.

Crushing at moderate peripheral speed therefore makes it possible to achieve better energy performance levels.

According to FIG. 6: Analyzing from the productivity angle, at a higher peripheral speed, a higher flow rate is obtained to reach the targeted degree of milling.

The productivity of a facility will be higher when the peripheral speed is increased.

In order to optimize an industrial facility, a compromise is to be defined between the operating expenses (OPEX) optimized at moderate peripheral speed and the capital expenditures (CAPEX) minimized at high peripheral speed.

Moreover, problems of abrasion of the milling disks and chamber and also bead-wear problems are to be considered since they may have a not insignificant economic impact on the process.

It is preferred to limit the peripheral speed to a value of less than 15 m/s (or even 13 m/s) in order to avoid excessive abrasion.

Cell Density

In addition to the physical parameters of the bead-milling facility, certain criteria regarding the biomass to be milled may have a not insignificant impact on the milling performance levels.

Thus, the impact of the cell concentration of the biomass on the milling performance levels is evaluated.

A biomass from the same production batch is prepared at several concentrations (20%, 25.2% and 32.9%).

The milling is carried out under the same conditions and the results are compared relative to the solids content of the samples thus generated.

According to FIG. 7: By analyzing relatively the impact of the cell concentration on the specific milling energy required to obtain a defined degree of milling, significant differences are demonstrated.

At high cell concentration, the specific energy consumed at a given degree of milling is much higher than at a lower cell concentration.

The milling of a cell biomass at a moderate concentration therefore makes it possible to achieve better energy performance levels than at a high concentration.

According to FIG. 8: Analyzing from the productivity angle, at high cell concentration, an equivalent facility will make it possible to pass a higher flow rate while at the same time achieving the targeted degree of milling.

In other words, the productivity of a facility will be higher when the cell concentration is increased.

Figure 1:
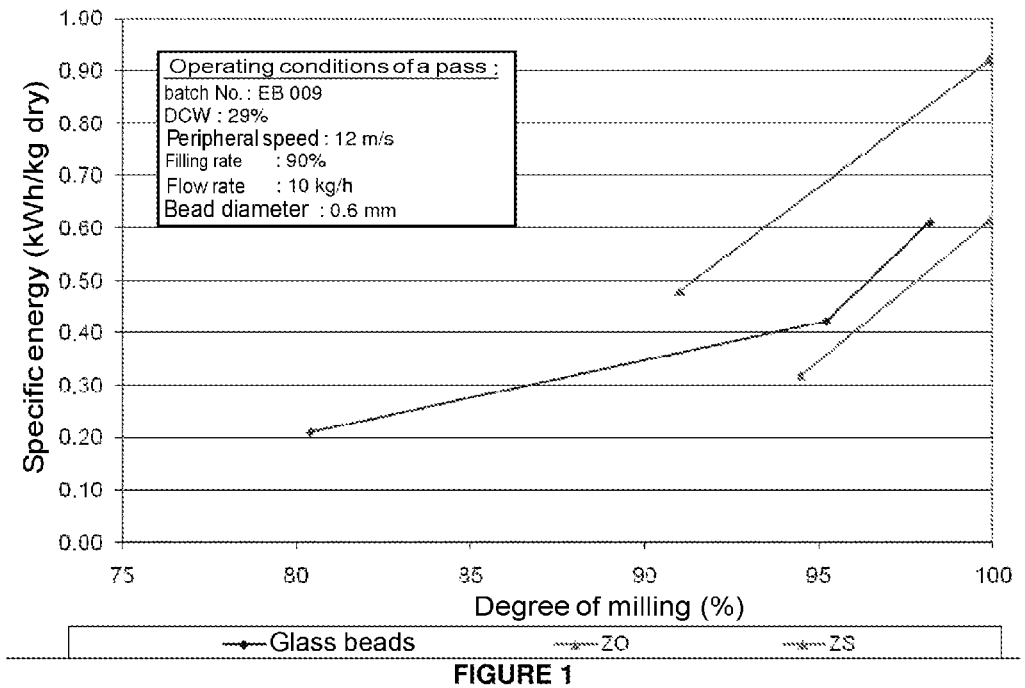
FIG. 1: Impact of the bead density (diameter 0.6 mm) on the milling performance levels
Figure 2:
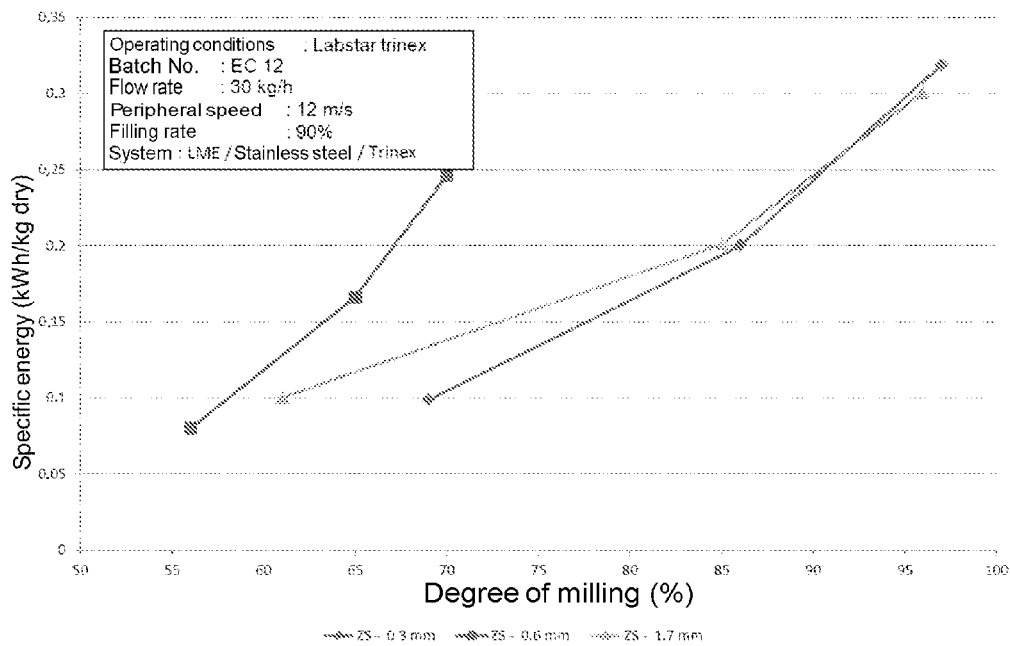
FIG. 2: Impact of the bead (ZS) diameter on the milling performance levels
Figure 3:
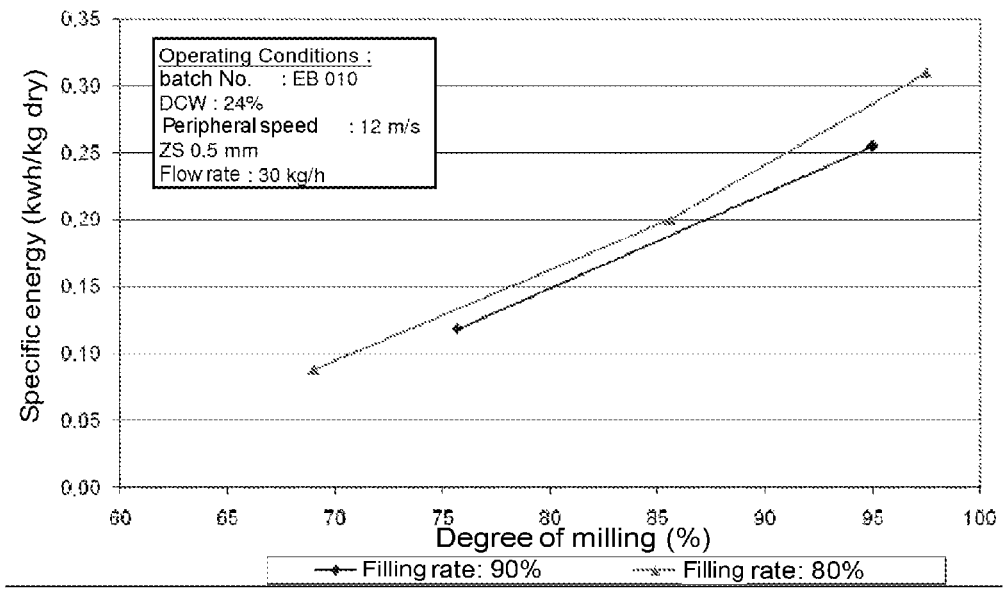
FIG. 3: Impact of the chamber filling rate on the milling performance levels
Figure 4:
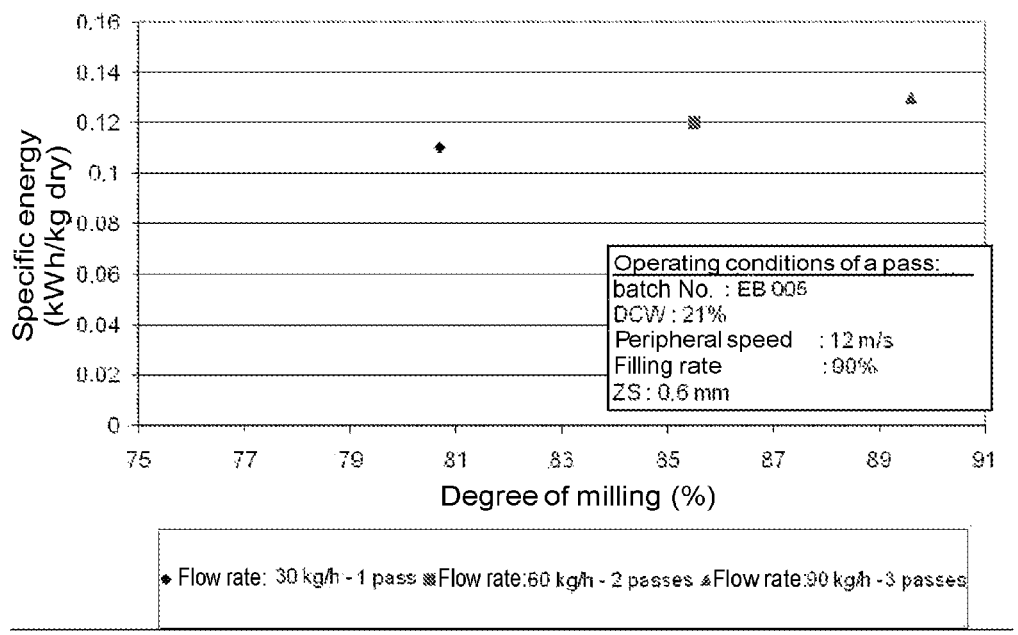
FIG. 4: Impact of the pass mode on the milling performance levels
Figure 5:
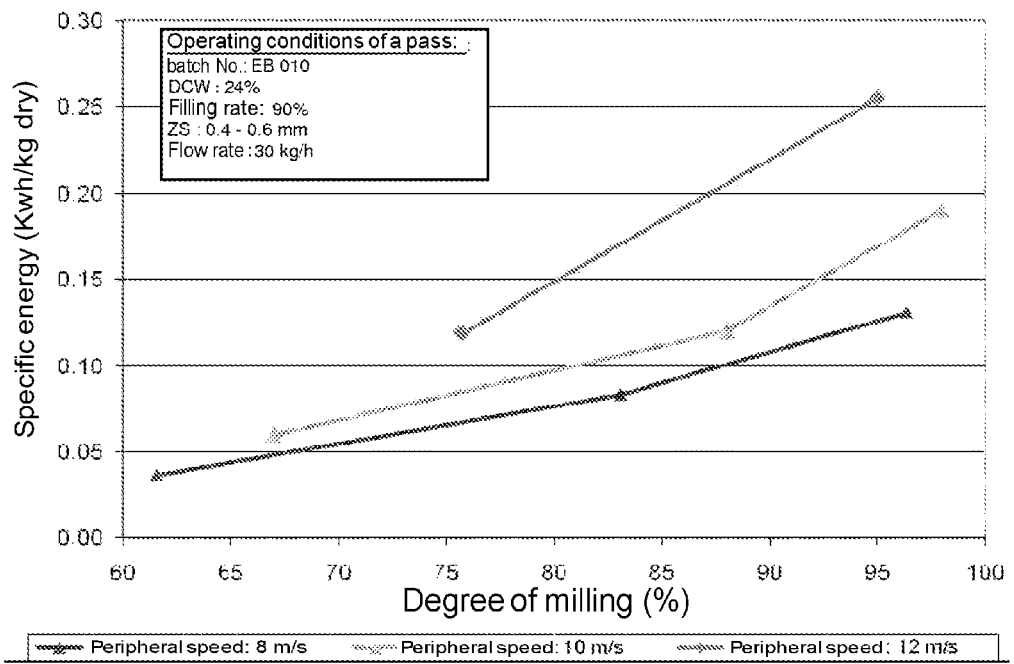
FIG. 5: Impact of the peripheral speed on the specific milling energy
Figure 6:
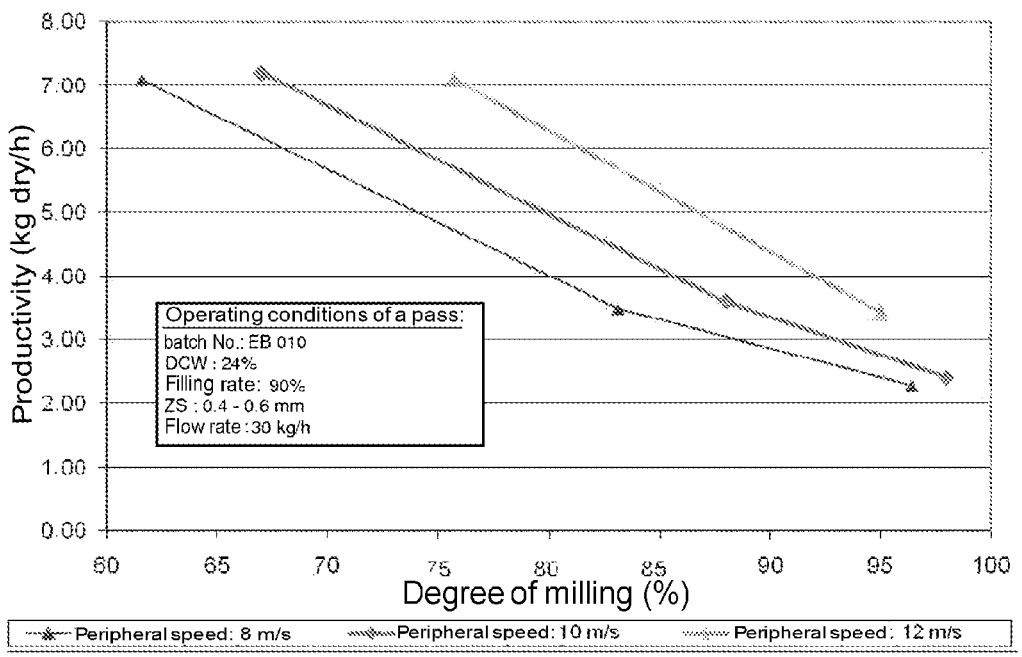
FIG. 6: Impact of the peripheral speed on the productivity of the milling operation
Figure 7:
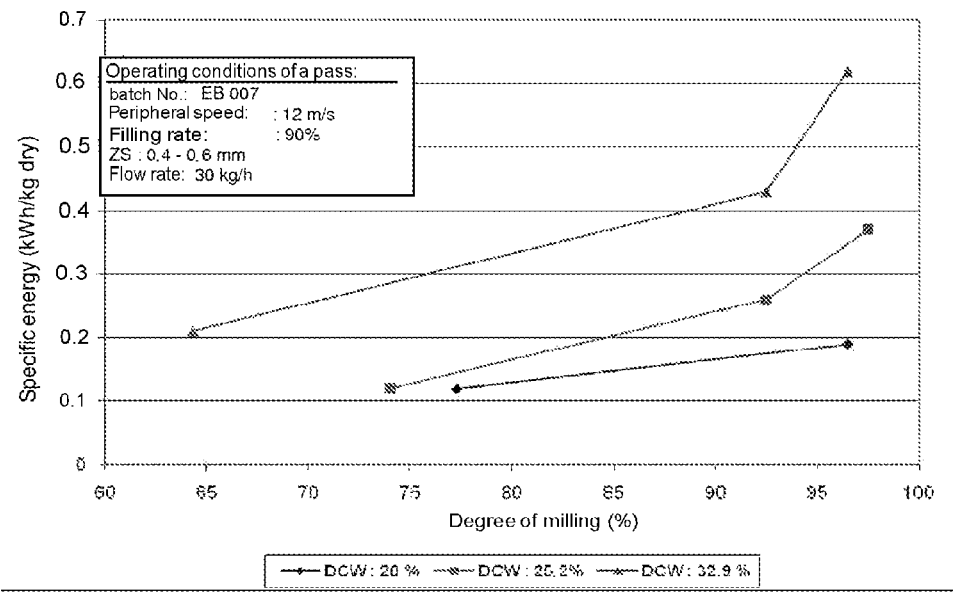
FIG. 7: Impact of the cell concentration on the specific milling energy
Figure 8:
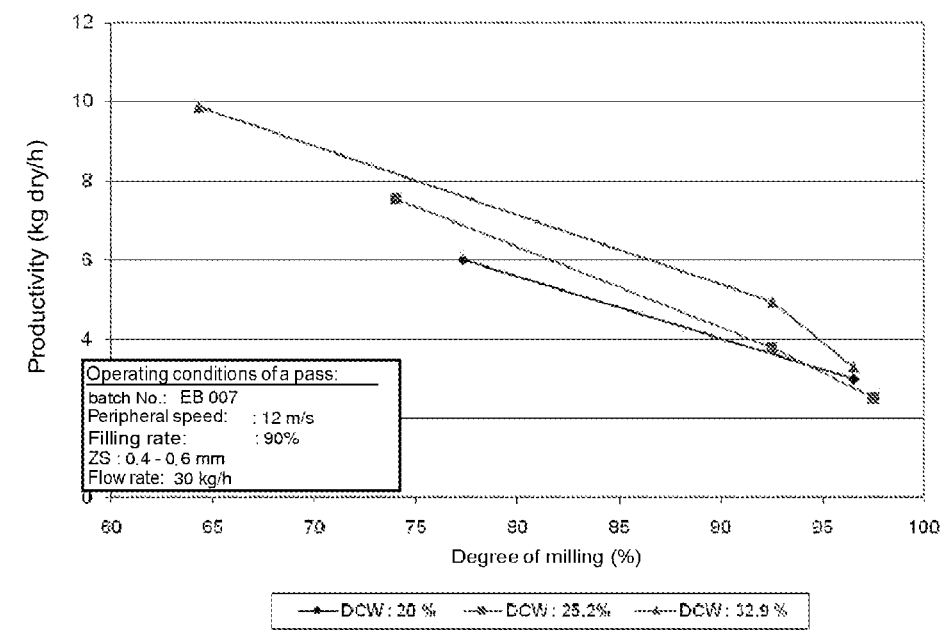
FIG. 8: Impact of the cell concentration on the productivity of the milling operation

The invention claimed is:

1. A process for the mechanical milling of cells of microalgae of the *Chlorella* genus, the mechanical milling being carried out in one or more horizontal bead mills, the one or more horizontal bead mills comprising zirconium silicate beads, wherein:
 the zirconium silicate beads have an apparent density of between 2 and 3.5 kg/l,
 a filling rate of a milling chamber of the one or more horizontal bead mills is greater than or equal to 80%, and wherein the mechanical milling is carried out in continuous mode by successive passes of said cells through said one or more horizontal bead mills.

2. The process of claim 1, wherein the microalgae of the *Chlorella* genus are selected from the group consisting of *Chlorella vulgaris*, *Chlorella sorokiniana*, and *Chlorella protothecoides*.

3. The process of claim 2, wherein the zirconium silicate beads have a diameter of less than 0.8 mm.

4. The process of claim 2, wherein the microalgae is *Chlorella protothecoides*.

5. The process of claim 1, wherein the zirconium silicate beads have a diameter of less than 1 mm.

6. The process of claim 1, wherein the filling rate of the milling chamber is greater than or equal to 85%.

7. The process of claim 6, wherein the microalgae of the *Chlorella* genus are selected from the group consisting of *Chlorella vulgaris*, *Chlorella sorokiniana*, and *Chlorella protothecoides*.

8. The process of claim 7, wherein the zirconium silicate beads have a diameter of less than 1 mm.

9. The process of claim 7, wherein the zirconium silicate beads have a diameter of less than 0.8 mm.

10. The process of claim 6, wherein the zirconium silicate beads have a diameter of less than 0.8 mm.

11. The process of claim 1, wherein the zirconium silicate beads have a diameter of less than 1 mm.

12. The process of claim 1, wherein the zirconium silicate beads have a diameter of less than 0.8 mm.

* * * * *